United States Patent [19]
Lee et al.

[11] Patent Number: 5,534,496
[45] Date of Patent: Jul. 9, 1996

[54] METHODS AND COMPOSITIONS TO ENHANCE EPITHELIAL DRUG TRANSPORT

[75] Inventors: Vincent H. Lee, Monterey Park, Calif.; Wan-Ching Yen, Columbus, Ohio

[73] Assignee: University of Southern California, University Park, Los Angeles, Calif.

[21] Appl. No.: 219,156

[22] Filed: Mar. 29, 1994

Related U.S. Application Data

[63] Continuation-in-part of Ser. No. 909,908, Jul. 7, 1992, abandoned.

[51] Int. Cl.$^6$ ............................................. A61K 38/08
[52] U.S. Cl. ........................ 514/17; 514/18; 514/19; 530/330; 530/331; 424/434
[58] Field of Search ................. 424/434; 514/17–19; 530/330, 331

[56] References Cited

U.S. PATENT DOCUMENTS 4,873,087  10/1989  Momishita ........................... 424/433

OTHER PUBLICATIONS

Yen, Proceed. Intern. Symp. Control. Rel. Bioact. Mater. 18, 95, 1991.

*Primary Examiner*—Christina Y. Chan
*Assistant Examiner*—David Lukton
*Attorney, Agent, or Firm*—Robbins, Berliner & Carson

[57] ABSTRACT

Methods and compositions provided for enhancing the transport of drugs (including peptides, oligonucleotides, proteins and conventional drugs) across epithelial cells at mucosal sites. The methods and compositions include the use of a peptide comprising at least two amino acids, such as Pro-Leu-Gly-Pro-Arg or Pro-Leu, and a protective group such as phenylazo-benzyloxycarbonyl, N-methyl, t-butyloxycarbonyl, fluoroenylmethyloxycarbonyl or carbobenzoxy, at the N-terminus, or in a mixture of such peptides in a sufficient amount to enhance the drug transport across epithelial cells at mucosal sites. Preferably, the peptide comprises 2 to 5 amino acids; the N-terminal amino acids are preferably Pro-Leu. The peptide with the drug are introduced to the mucosal site in a physical mixture, a conjugated form or by a microcapsule, microsphere, liposome, cell, bacteria, virus or food vesicle carrier by an oral, nasal, pulmonary, buccal, rectal, transdermal, vaginal or ocular route.

8 Claims, 11 Drawing Sheets

VMAX, NMOLE/MIN/MG PROTEIN

PAPP (E-05, CM/SEC)

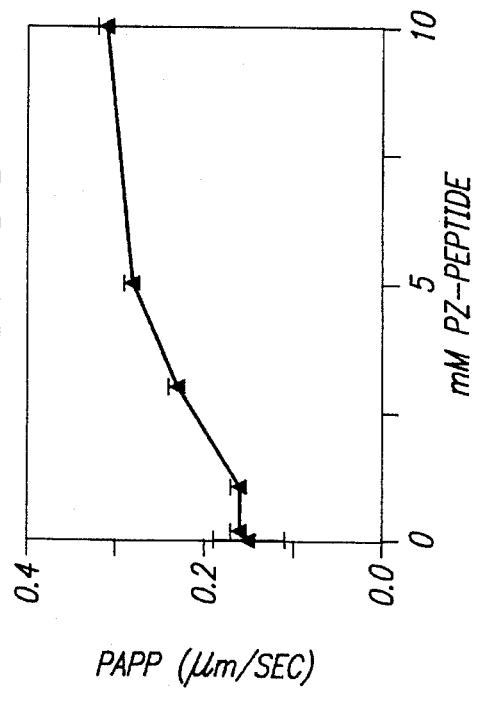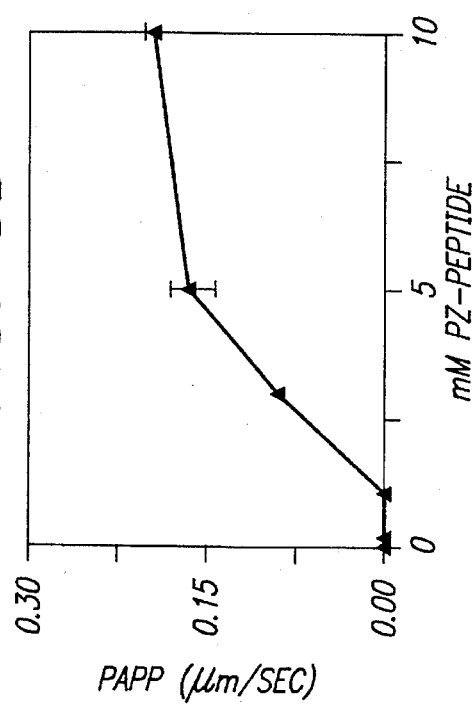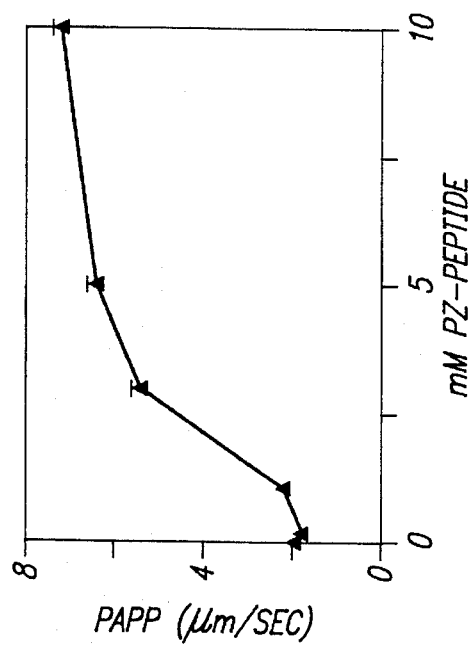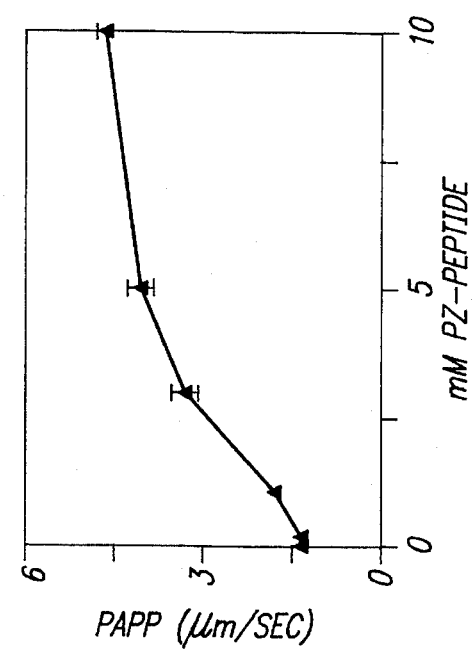

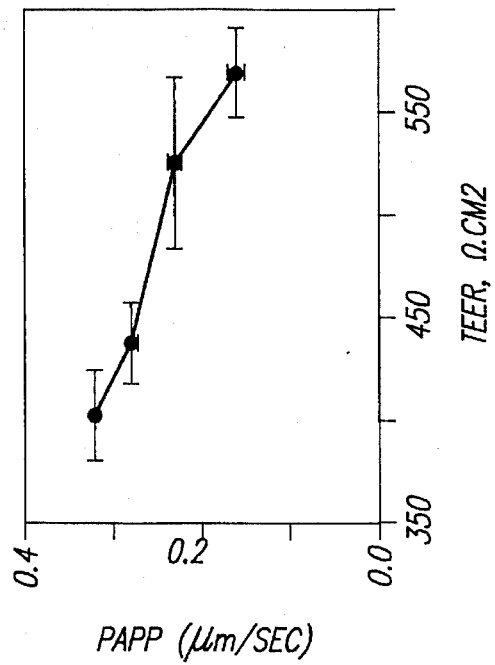
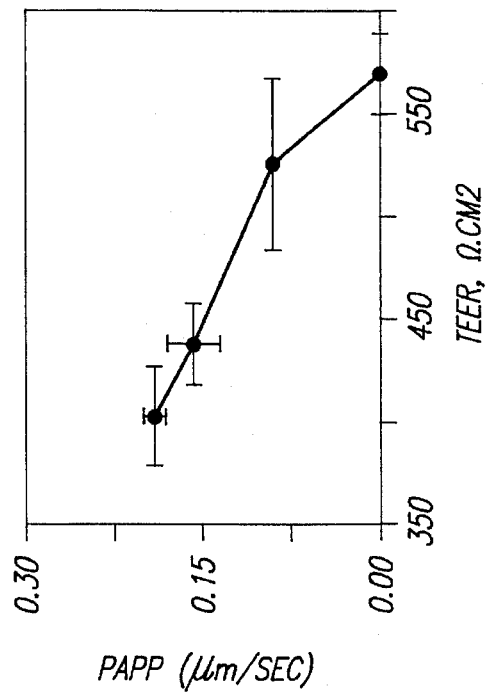
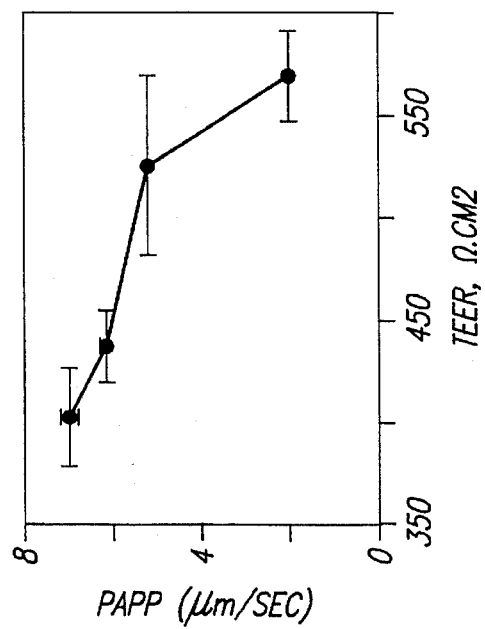
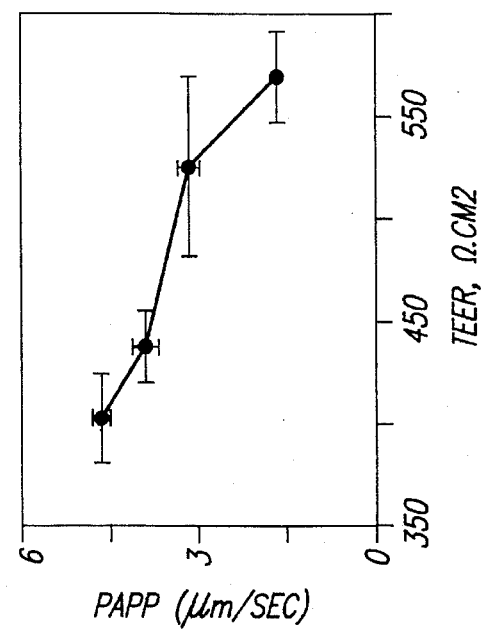

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:1:

Xaa  Leu  Gly  Pro  Xaa
    1                           5

( 2 ) INFORMATION FOR SEQ ID NO:2:

( i ) SEQUENCE CHARACTERISTICS:
    ( A ) LENGTH: 5 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:2:

Pro Leu Gly Pro Xaa
  1       5

( 2 ) INFORMATION FOR SEQ ID NO:3:

( i ) SEQUENCE CHARACTERISTICS:
    ( A ) LENGTH: 5 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:3:

Pro Leu Glu Pro Xaa
  1       5

( 2 ) INFORMATION FOR SEQ ID NO:4:

( i ) SEQUENCE CHARACTERISTICS:
    ( A ) LENGTH: 5 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:4:

Pro Leu Gly Pro Arg
  1       5

( 2 ) INFORMATION FOR SEQ ID NO:5:

( i ) SEQUENCE CHARACTERISTICS:
    ( A ) LENGTH: 4 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:5:

Pro Leu Gly Pro
  1

( 2 ) INFORMATION FOR SEQ ID NO:6:

( i ) SEQUENCE CHARACTERISTICS:
    ( A ) LENGTH: 5 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:6:

Pro Leu Gly Pro Lys
  1       5

( 2 ) INFORMATION FOR SEQ ID NO:7:

( i ) SEQUENCE CHARACTERISTICS:
    ( A ) LENGTH: 5 amino acids

```
            ( B ) TYPE: amino acid
            ( D ) TOPOLOGY: linear ( i i ) MOLECULE TYPE: peptide ( x i ) SEQUENCE DESCRIPTION: SEQ ID NO:7:

Pro   Leu   Gly   Pro   Glu
    1                       5

( 2 ) INFORMATION FOR SEQ ID NO:8:

( i ) SEQUENCE CHARACTERISTICS:
            ( A ) LENGTH: 5 amino acids
            ( B ) TYPE: amino acid
            ( D ) TOPOLOGY: linear ( i i ) MOLECULE TYPE: peptide ( x i ) SEQUENCE DESCRIPTION: SEQ ID NO:8:

Pro   Leu   Gly   Pro   Asp
    1                       5
```

METHODS AND COMPOSITIONS TO ENHANCE EPITHELIAL DRUG TRANSPORT

RELATED APPLICATION

This application is a continuation-in-part application of prior application Ser. No. 07/909,908, filed on Jul. 7, 1992, now abandoned.

BACKGROUND OF THE INVENTION

1. Field of the Invention

The present invention relates to methods and compositions which enhance the epithelial transport of drugs (including peptides, oligonucleotides, proteins and conventional drugs) that are subject to extensive breakdown within epithelial cells in various mucosal sites, such as the gastrointestinal tract. Particularly, the methods and compositions enhance the transport of drugs in most therapeutic categories, such as anti-infective, antiviral, centrally acting, cardiovascular, respiratory, cholesterol reducing, anticancer, imaging, antidiabetic, immunomodulating, antineoplas-tics, antiinflammatory, oral contraceptive and the like, across epithelial cells. More specifically, the present invention is directed to using a peptide of at least 2 amino acids, preferably of two to five amino acids. The N-terminal amino acids are preferably Pro-Leu, having a protective group, such as phenylazobenzyloxycarbonyl (Pz-group,

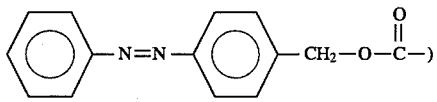

)
N-methyl, t-butyloxcarbonyl (t-Boc), fluoroenylmethyloxycarbonyl (FMOC) or carbobenzoxy (CBZ), at the N-terminus. If the peptide has more than 4 amino acids, a charged amino acid such as Arg, Lys, Glu or Asp at the C-terminus, transiently and reversibly enhances the transport of drugs across epithelial cells. The mechanism is believed to involve increasing the permeability of tight junctions between epithelial cells through activation of ion transport channels, such as sodium channels on the cell membrane. The protected peptide can be used alone or in a mixture to enhance the transport of drugs across the epithelial cells.

More specific objectives and advantages of the invention will hereinafter be made clear or become apparent to those skilled in the art during the course of explanation of preferred embodiment of the invention.

2. Description of the Prior Art

The entry of high molecular weight active agents (such as peptides, proteins and oligonucleotides) and conventional drugs (such as mannitol, atenolol, fluorescein, insulin, vasopressin, leucine enkephalin, Asu-eel calcitonin, 5-fluorouracil, salicylamide, β-lactones, ampicillin, penicillins, cephalosporins, β-lactamase inhibitors, quinolones, tetracyclines, macrolides, gentamicin, acyclovir, ganciclovir, trifluoropyridine and pentamidine) through mucosal routes (such as oral, nasal, pulmonary, buccal, rectal, transdermal, vaginal and ocular) to the bloodstream is frequently obstructed by poor transport across epithelial cells and concurrent metabolism during transport. Penetration enhancers (substances that facilitate the transport of solute across biological membranes) have been well investigated for the last five decades as reported by Lee et al. (Vincent H. Lee, Akira Yamamoto, and Udaya Bhaskar Kompella, Critical Reviews in Therapeutic Drug Carrier Systems, Vol. 8, No.2, pp. 91–192 (1991), the disclosure of which is herein incorporated by reference). Penetration enhancers are broadly divided into five groups: (1) chelators, e.g. EDTA; (2) surfactants, e.g. sodium lauryl sulfate; (3) bile salts and derivatives, e.g. sodium deoxycholate; (4) fatty acids and derivatives, e.g. oleic acid; and (5) non-surfactants, e.g. unsaturated cyclic ureas. While the penetration enhancers enhance the permeability of the epithelial cell, thereby facilitating the transport of drugs across biological membranes, they also raise a number of pressing safety concerns, such as irritation of mucosal tissues, damages in the mucosal cells, poor damage recovery rates and alterations in mucociliary clearance (Lee et al. at p. 140).

Other approaches, such as co-administration of protease inhibitors, e.g. bacitracin, aprotinin, amastatin, bestatin, and puromycin (Lee et al. at p. 92), modification of peptide, protein and antibodies structures, (U.S. Pat. No. 5,004,697 to Pardridge), and the use of formulations changes, such as pH, tonicity and the use of solubilizers (Lee et al. p. 167) have been reported. In addition, iontophoresis (transfer of ionic solutes through biological membranes under the influence of an electric field) (Lee et al. at p. 163), phonophoresis or sonophoresis (use of ultrasound to enhance the absorption of various therapeutic agents across biological membranes notably the skin and the cornea) (Lee et al., at p. 166) and optimization of vehicle characteristics relative to dose deposition and retention at the administration site (Lee et al., p. 168) have also been tried to enhance the transport of drugs across mucosal sites.

Although these approaches have experienced some success, they have not been entirely successful, either because of safety concerns (e.g. use of existing enhancers), or because they involve ineffective, inefficient, inconvenient and difficult techniques in various applications (e.g. chemical modifications, iontophoresis and phonophoresis). In addition, these approaches failed to protect, specifically, peptide and protein drugs from proteases beyond the lumen if the drug is administrated through the oral route.

There presently is a great need to provide convenient and simple methods and compositions to enhance the epithelial transport of drugs at various mucosal sites. It is desirable that such new methods and compositions provide for a simple, convenient, practical and optimal introduction of drug transport and delivery across epithelial cells at various mucosal sites with as few safety concerns to the patient as possible.

SUMMARY OF THE INVENTION

In accordance with the present invention, new methods and compositions are described which provide a simple, convenient, practical and optimal introduction of drug transport and delivery across epithelial cells at various mucosal sites while reducing the safety concern to the patient.

The present invention is based on the surprising discovery that certain peptides, such as Pz-Pro-Leu and Pz-Pro-Leu-Gly-Pro-D-Arg (hereinafter "Pz-peptide [SEQ.ID NO:1]"), can be used to transiently and reversibly enhance the permeability of tight junctions between cells by activating ion channels such as sodium channels on the cell membrane. In general, the peptide comprises at least 2 amino acids, preferably about 2–5 amino acids; the amino acids are preferably Pro-Leu at the N-terminal end. The peptide also has a protective group, such as phenylazobenzyloxycarbonyl (Pz), N-methyl (Roemer, D., Huescher, H. H., Hill, R. C., Pless, J., Bauer, W., Cardinaux, F., Closse. A., Hauser, D. and Huguenin, R. (1977), Nature, Vol. 268, pp. 547–749), t-butyloxcarobonyl (t-Boc) (Morita, T. et al. (1977) J. Biochem 82:1495); fluoroenylmethyl-oxycarbonyl (FMOC) (Atherton E., D. L. J. Clive and Sheppard, R. C. (1975) J. Am. Chem. Soc. 97:6584); and carbobenzoxy (CBZ) (Nagai, Y. Sakakibara, S., Noda, H. and Akabori, S. (1960) Biochim. Biophys. Acta. 37: 567–569) at the N-terminus. The peptide further has a charged amino acid, such as D-Arg, Lysine, Glu or Asp at the C-terminus, if the peptide has more than 4 amino acids. The discovery is particularly surprising in view of the test results that although collagenase activity was highest in the descending colon, the Pz-peptide and Pz-Pro-Leu penetrated very well in this region. For the Pz-peptide, after penetration, 80% of it remains in the intact form.

The invention involves the use of a single peptide or a mixture thereof, containing a N-protective group and if the peptide has more than 4 amino acids, a charged amino acid at the C-terminus either in physical mixture with the drug whose transport is to be enhanced, or in conjunction with the drug via a chemical linkage such as peptide bond, that will be cleaved in the bloodstream and/or other sites within the body. It is well known to one skilled in the art how to chemically link a drug to a peptide, such as poly-D-lysine, poly-L-aspartic acid and poly-(2-hydroxyethyl)-D,L-asparagine. The chemical linkage will result in drug carriers for methotrexate, daunorubicin and trypsin-kallikrein inhibitor, which are long known to one skilled in the art (see Ryser, H. J-P, and Shen, W. C. (1978) Proc. Natl. Acad. Sci. USA 75:3867; Zunino, F., Giulliani, F., Savi, G., Dasdia, T., and Gambetta, R. (1982) Int. J. Cancer 30:465; Havranova, M., Cschova, D., Saudek, V., Metalova, M. and Drobnik, J. (1982) Hoppe-Sayler's Z. Physiol. Chem. 363:295; Zunino, F., Savi, G., Giuliani, F., Gambetta, R., Supino, R., Tinelli, S. and Pezzoni, G. (1984) Eur. J. Cancer Clin. Oncol. 20:421). Moreover, in most of these chemically-linked drugs, the drug maintains its activity.

Other methods to conjugate a drug is to have it as part of the external surfaces of colloidal carriers such as microcapsules, microspheres, liposomes, cells, food vesicle, nanoparticles, bacteria, viruses or the like. Colloidal carriers are well known to one skilled in the art (Juliano, R. L.: Microparticulated drug carriers: liposomes, microspheres and cells, in "Controlled Drug Delivery" Robinson J. R. and Lee. V. H. L. eds. Marcel Dekker Inc. N.Y. Ch.13.; Widder, K. J. and Senyei, A. E. (1983) Pharm. Ther. 20:377–396). To one skilled in the art, colloidal carriers are microparticulate drug-carrier systems with diameter ranging from 25 nm to 10 μm. This is shown by the example of nasal microspheres by Bjork and Edmon ("Degradable starch microspheres as a nasal delivery system for insulin", Intern. J. of Pharm., Vol. 47, pp. 233–238 , 1988) to enhance the nasal absorption of insulin. The disclosure of this reference is herein incorporated by reference to show that the Pz-peptide would be physically incorporated in the microspheres following the method described by Bjork and Edmon for application locally. The Pz-peptide is expected to be released either immediately before or simultaneously with the release of the entrapped therapeutic peptide.

Liposomes, microsphere and cells are the three main groups of colloidal carriers. Juliano, R. B. at p. 560 (1983) illustrates the preparation of various microparticulate drug carriers. Bacteria and virus belong to the category of cells. To one skilled in the art, the advantages of using cells, bacteria and virus are that, when suitably modified, they are non-toxic, biocompatible and rapidly eliminated by the phagocytic cells located in the liver and spleen once the drug is released. Also, the term "food vesicle" means a biodegradable polymer-based microsphere such as polymerized albumin and lipoproteins. Particles range smaller than 100 nm are termed nanoparticles. The present invention is not directed to new colloidal carriers, rather it is the use of this new Pz-peptide in known colloidal carrier systems to enhance drug transport.

Methods to conjugate the drug with the Pz-peptide are well-known. U.S. Pat. No. 4,902,505 to Pardridge et al., the disclosure of which is herein incorporated by reference, describes the conjugation carried out using bi-functional reagents such as N-succinimidyl 3-(2-pyridyldithio) propionate (SPDP) to form a disulfide bridge. In Example 1 of U.S. Pat. No. 4,902,505, somatostatin and insulin were conjugated by peptide thiolation using a reversible peptide-peptide conjugation method as described by Carlsson, et al., in "Protein Thiolation and Reversible Protein-Protein Conjugation" (Biochem. J. (1987) 173, 723–737). According to this method, a heterobiofunctional agent, N-succinmidyl-3-(2-pyridyldithio)-propionate(SPDP), was used to couple a lysine or free-N-terminus on insulin to a free lysine or amino terminus on somatostatin. The detailed procedure for the chemical linking was also clearly laid out in the example. This method is clearly applicable to the present invention in coupling a Pz-peptide, such as Pro-Leu-Gly-Pro-Lys [SEQ ID NO:6] to insulin. While the Pz-peptide of the present invention is found to have the unique property of enhancing the epithelial transfer of drugs, its chemistry in coupling with drugs remains essentially based on its peptide properties. Other conjugation reagents include glutaraldehyde and cystamine and EDAC.

BRIEF DESCRIPTION OF THE DRAWINGS

The above discussed novel features, advantages, characteristics of the invention are set forth with particularity in the appended claims. The invention itself, however, both as to its methods and compositions, may best be understood by reference to the following detailed description taken in connection with the accompanying drawings, and in which:

FIGS. 8A–8D show concentration dependence of $P_{app}$ of mannitol (FIG. 8A), atenolol (FIG. 8B), fluorescein (FIG. 8C) and FITC-dextran 4,000 (FIG. 8D) described in Example 6. Error bars represent s.e.m. for n=3;

FIGS. 9A–9D show the correlation between transepithelial electrical resistance (TEER) and extent of penetration (Papp) of mannitol (FIG. 9A), atenolol (FIG. 9B), fluorescein (FIG. 9C) and FITC-dextran 4,000 (FIG. 9D) described in Example 6. Error bars represent s.e.m. for n=3;

(FIG. 11A) and 2 hours (FIG. 11B), all at 3 mM described in Example 8. Key: Δ, Pz-peptide; □, EDTA; ●, cytochalasin B. Error bars represent s.e.m. for n=3;

DETAILED DESCRIPTION OF THE PREFERRED EMBODIMENT

Figure 1:
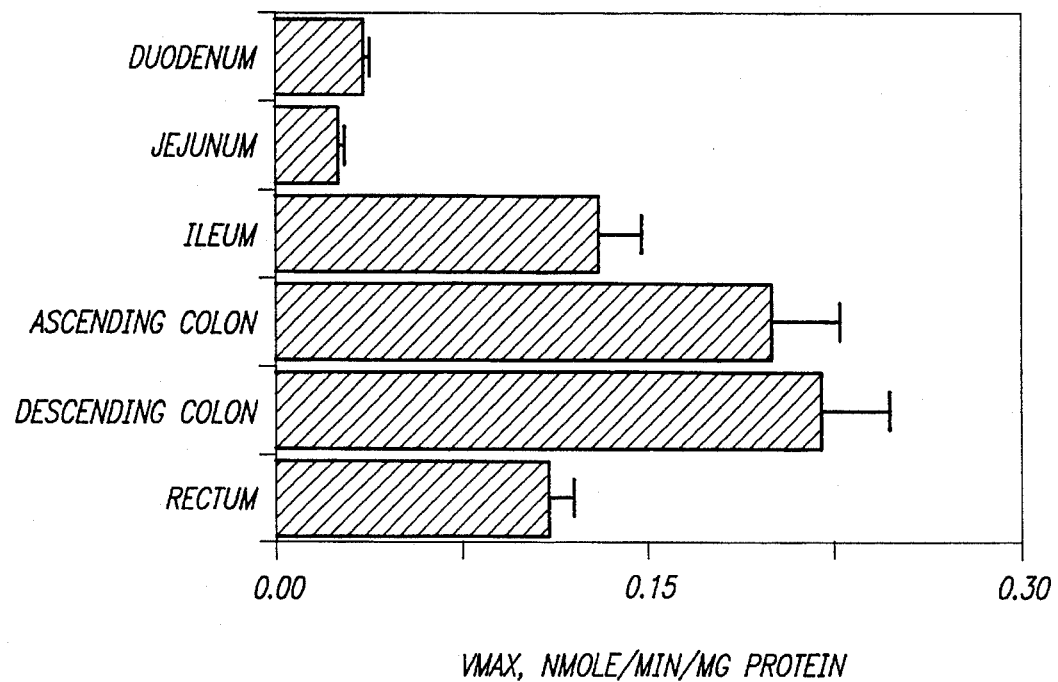
FIG. 1 shows collagenase activity measured in terms of maximum velocity (Vmax) of Pz-peptide hydrolysis in cytosolic fraction in various intestinal segments described in Example 2. Error bars represent s.e.m. for n=3.

The present invention provides a peptide with a protective group, such as Pz, t-Boc, FMOC or CBZ at the N-terminus and if the peptide has more than 4 amino acids, a charged amino acid, such as a D-Arg, Lys, Glu and Asp at the C-terminus transiently and reversibly enhances the transport of drugs.

The peptides used in the examples herein are commercially available from Bachem, Inc. (Torrance, Calif.). These and other peptides can also be prepared according to the procedures reported by Wunsch et al. (Wunsch, E. and Heidrich, H. G. (1962) Hoppe-Seylers Z. Physiol. Chem. Vol. 332, page 300–304, the disclosure of which is incorporated herein by reference).

The regional distribution of collagenase-like activity in the albino rabbit as well as the influence of collagenase-like activity on the intestinal penetration of Pz-peptide, a collagenase substrate was determined. Both collagenase and collagenase-like enzymes are terms well known to one skilled in the art. They are both metalloproteases that are responsible for collagen breakdown. Further, these two enzymes differ in several ways. First, using Pz-peptide as a substrate, the Km and Vmax for collagenase-like enzyme are 0.2 mM and 4 μmol/min/mg protein, respectively (Evans, C. H., Biochem J. (1981) 195:677–684), where the Km and Vmax for collagenases are 5 mM and 0.3 μmol/min/ml/mg. protein respectively. Secondly, the collagenase-like enzymes are restricted to degradation of collagen products with 5 to 30 residues (Morales, T. et al., J. Biol. Chem (1977) 252:4855–4860). Finally, collagenase-like enzymes are latent in the physiological condition but their level is high in tissue modeling processes (Aswanikumar, S. et al., Biochem. Biophys. Acts (1972) 276:241–249; Sakyo, K. et al., J. Biochem. (1983) 94:1913–1923, Rajabi, M. et al., Am. J. Obsetet. Gynecol. (1984) 150:821–826).

A. Determination of Collagenase Activity in Homogenates and Subcellular Fractions Collagenase activity in homogenates and subcellular fractions of the gastrointestinal mucosa of the albino rabbit was determined by incubating 30 μl a homogenate or subcellular fraction with 20 μl of a Pz-peptide solution in 11% ethanol for up to 60 min. The subcellular fractions were the cytosolic and membrane fractions, and the concentrations of Pz-peptide ranged from 0.1 to 2 mM. The reaction was stopped by adding 225 μl of acetonitrile to the incubation mixture. Following centrifugation to remove precipitated proteins, an aliquot of the supernatant was injected into the HPLC for assay of the intact peptide and its hydrolytic product, Pz-L-Pro-L-Leu. Collagenase activity was determined from the initial slope of a plot of product concentration vs. time.

B. Evaluation of Intestinal Transport of Pz-peptide

The penetration of Pz-peptide across the isolated segments of duodenum, jejunum, ileum, ascending colon, descending colon, and rectum of the albino rabbit was evaluated in the modified Ussing chamber. Solution of Pz-peptide at concentrations of 1, 3, and 5 mM were prepared in 5% hydroxypropyl β-cyclodextrin, which was found not to affect either collagenase activity or integrity of the intestinal segments. Periodically up until 240 min, a 50 μl aliquot was collected from the serosal side and injected directly into the HPLC. The apparent permeability coefficient $P_{app}$, was calculated using methods well known to one skilled in the art. $P_{app}$ is defined as the flux of any solute transported across a given membrane per unit area normalized to the concentration applied (see pages 72–73 from the text by W. D. Stein entitled, "Transport and Diffusion A Cross Cell Membranes"). In this case, the $P_{app}$ for Pz-peptide referenced in FIG. 2 was calculated from the slope of the linear portion of a plot of Pz-peptide concentration on the receiver side vs time normalized to the initial Pz-peptide concentration on the donor side.

C. Evaluation of Pz-peptide's effect on paracellular permeability in human colon carcinoma cell monolayer (Caco2)

The effect of Pz-peptide on extent of paracellular permeability was further studied in human carcinoma cell monolayer (Caco2) due to its high degree of differentiation into polarized columnar cells (Rousset, M., Labruthe, M., Pinto, M., Chevalier, G., Rouyer-Fesard, C., Dussaulx, G., Truganan, N., Boige, N., Burn, J. L. and Zweibaum, A. (1985) J. Cell Physiol. Vol. 123, p. 377); exhibition of well-developed microvilli (Pinto, M., Robine-Leon, S., Appay, M. D., Kidinger, M., Triadov, N., Dussaulx, E., Lacroix, B., Simon-Assmann, P., Hoffen, K., Fogh, J. and Zwiebaum, A. (1983) Biol. Cell, Vol. 47, p. 323) and polarized distribution of several brush border enzymes, (Hauri, H. P., Strerchi, E. E., Bienz, D., Fransen, A. M. and Marker, A. (1985), J. Cell Biol. Vol. 101, page 838). Cell culture protocols were adapted from Hidalgo, et al. (Hidalgo, I. J., Raub, T. J. and Borchard, R. T. (1989) gastroenterology, Vol. 96, p. 736)). A 500 ohms·cm$^2$ transepithelial electrical resistance, TEER, was used for the study.

The experiment was initiated by replacing the mucosal solution with sample solution. The viability of the cell monolayers was measured by TEER before and after exposure to the peptide solution. Five paracellular markers with different molecular radii were used to determine the extent of enhancement. All markers: mannitol (3.6 Å), atenolol (3.8 Å), fluorescein (5.5 Å), FTIC-dextran 4,000 (FD04, 14 Å), FITC-dextran 10,000 (FD10, 22 Å) were purchased from Sigma (St. Louis, Mo.) the $P_{app}$ for atenolol referenced in FIG. 6 and 7 was calculated from the slope of the linear portion of a plot of atenolol concentration on the receiver side vs. time normalized to the initial atenolol concentration on the donor side; whereas the $P_{app}$ for mannitol referenced in FIGS. 6 and 7 was calculated from the slope of the linear portion of a plot of mannitol concentration on the receiver side vs. time normalized to the initial mannitol concentration on the donor side. Similarly, the $P_{app}$ for fluorescein referenced in FIGS. 7 and 8 was calculated from the slope of the linear portion of a plot of fluorescein concentration on the receiver side vs. time normalized to the initial fluorescein concentration on the donor side; whereas the $P_{app}$ for FITC-dextran 4,000 referenced in FIG. 7 and 8 was calculated from the slope of the linear portion of a plot of FITC-dextran 4,000 concentration on the receiver side vs. time normalized to the initial FITC-dextran 4,000 concentration on the donor side. Finally, the $P_{app}$ for FITC-dextran 10,000 referenced in FIG. 7 was calculated from the slope of the linear portion of a plot of FITC-dextran 10,000 concentration on the receiver side vs. time normalized to the initial FITC-dextran 10,000 concentration on the donor side.

D. Measurement of distribution coefficient (DC) of peptides

The distribution coefficient (DC) of Pz-peptide and Pz-Pro-Leu were determined in n-octanol/0.05 M phosphate buffer, pH=7.4, at 22±° C. Samples from both phases were withdrawn and the concentrations of Pz-peptide and Pz-Pro-Leu were determined by measuring the absorbance of the supernatant by a UV spectrometer.

E. Evaluation of the effect of the Pz-group

To further demonstrate the importance of the Pz-group at the N-terminus in facilitating the peptide transport, penetration of Pro-Leu, PLGP$^d$R (Pro-Leu-Gly-Pro-$^d$Arg) [SEQ ID NO: 2] and PLEP$^d$R (Pro-Leu-Glu-Pro-$^d$Arg) [SEQ ID NO: 3] were tested in Caco2 monolayers. All Pz-peptide analogues were synthesized by solid phase peptide synthesis method (G. Barany and Merrifield, R. B. in "The peptides" Vol. 2 (Gross E. and Meienhofer, J. eds), Academic Press, N.Y. (1979) pp. 1–284). This method involved the attachment of an α-amino-protecting, side-chain-protected amino acid, tert-butyloxycarbonyl (t-Boc) amino acid, to an insoluble polymeric solid support. The amino protecting group was then mechanically removed (deprotection), any salt of the amino component was converted to a free amine by reaction with a weak organic base (neutralization). An excess of the next amino acid was added and allowed to react with the amine in the presence of an activating reagent such as dicyclohexylcarbodiimide (DCC) to form the first peptide bond (coupling). The solvents and any excess reagents were filtered from the insoluble peptide-resin and this process of deprotection, neutralization and coupling was repeated until the final peptide sequence was completed. The peptide-resin was then treated with liquid hydrofluoric acid to remove the peptide from the solid support and to remove the side-chain protecting groups. Approximately 100 mg of crude peptide was delivered. The product was characterized by amino acid analysis and an analytical HPLC chromatogram.

F. Pharmaceutical composition with enhanced epithelial drug transport

The Pz-peptide of the present invention can be used to enhance transport of drugs, such as mannitol, atenolol, fluorescein, insulin, vasopressin, leucine enkephalin, [Asu] -eel calcitonin, 5-fluorouracil, salicylamide, β-lactones, ampicillin, penicillins, cephalosporins, β-lactamase inhibitors (such as cefazalin, cephalexin, cephaloridine and cephalothin, Merck index, 4th Ed. 1992), quinolones, tetracyclines, macrolides, gentamicin, acyclovir, ganciclovir, trifluoropyridine, and pentamidine, through epithelial cells by mucosal routes, such as oral, nasal, pulmonary, buccal, rectal, transdermal, vaginal and ocular routes.

The amount of Pz-peptide used with a drug in a composition at any one time will increase the specific drug transport sufficiently to provide a beneficial clinical result. Later concentrations of Pz-peptide used can be adjusted in accordance with clinical enhancement effect of the initial concentration. A typical initial amount of Pz-peptide used in the composition is to provide a concentration of Pz-peptide of not more than 6 mM at the epithelial cells. The Pz-peptide/ drug ratio depends on the specific drug used. Typically, a Pz-peptide/drug ratio used is in the range of 1:10 to 1:1000, preferably, the range is from 1:50 to 1:250, most preferably about 1:100. Thus, for a typical drug composition, with about 10–1000 mg of drug used in an average human, the amount of peptide used will be about 0.01–100 mg, preferably 0.04–20 mg, and most preferably about 0.1–10 mg. The total daily dose can consist of a single individual dose or multiple doses of the Pz-peptide/drug composition given at intervals.

Pharmaceutical compositions can include, in addition to the drug and the Pz-protected peptide, various inert carriers and/or other inactive components such as solubilizers (cyclodextrins), moistening agents, flavors, binding agents, and extenders, as well as other compounds having pharmacological activities.

The pharmaceutical compositions can take the form of tablets, capsules, oral solutions, nasal spray, aerosol, suppositories and other formulations intended for pharmaceutical use via the mucosal route. For example, a composition intended for use in a tablet contains 25 mg of the drug, 0.4 mg of the Pz-protected peptide, 5-hydroxypropyl β-cyclodextrin, calcium stearate, calcium sulfate, microcrystalline cellulose, peppermint oil, polysorbate 80, povidone, and pregelatinized starch.

In addition, to optimize the enhancement of drug transport, the tablet may be formed with the drug trapped inside a uniform coating of the Pz-protected peptide in a cyclodextrin matrix. Thus, when the tablet entered the mucosal route, the peptide in the cyclodextrin matrix will first be dissolved to provide opening of the ion transport channels, such as the sodium channel, followed by the drug being released from the tablet and transported across the epithelial cells.

Further to the use in human, the Pz-protected peptides of the invention can be used for similar veterinary purposes in domesticated animals to enhance drug transport.

The invention will be better understood with reference to the following examples which are intended for purposes of illustration and are not to be construed as in any way limiting the scope of the present invention, which is defined in the claims appended hereto.

EXAMPLE 1

Determination of collagenase activity

Using the procedure described in section A above, collagenase actively for the Pz-peptide was found in both tissue homogenate and subcellular fractions of the intestinal segments of the albino rabbit. Referring to FIG. 1, collagenase-like activity was highest in the descending colon and lowest in the jejunum, there being a 7-fold difference in activity at both high and low substrate concentration. The rank order was descending colon>ascending colon>rectum>ileum>duodenum>jejunum. About 60% of collagenase-like activity was in the cytosol.

EXAMPLE 2

Determination of intestinal transport of the Pz-peptide

Figure 2:
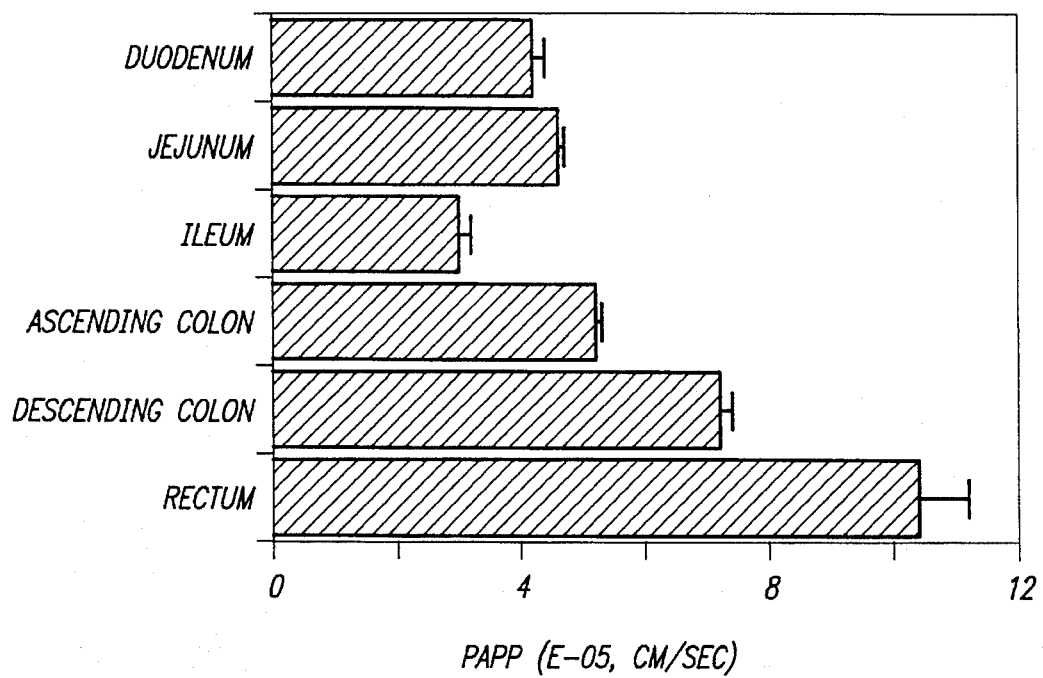
FIG. 2 shows the result of Pz-peptide penetration (Papp) at 5 mM measured in various intestinal segments described in Example 3. Error bars represent s.e.m. for n=3.
Figure 3A:
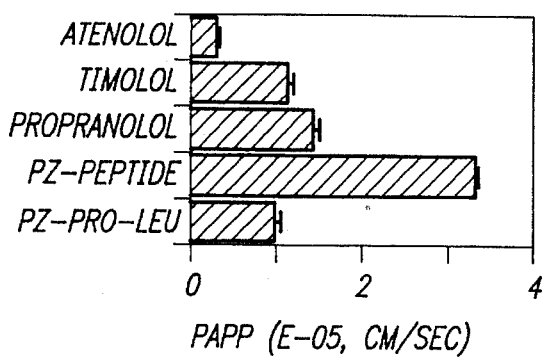
FIGS. 3A–3F show the results of the penetration of Pz-peptide and Pz-Pro-Leu relative to those of atenolol, timolol and propranolol, all at 3 mM described in Example 3. Error bars represent s.e.m. for n=3.
Figure 3D:
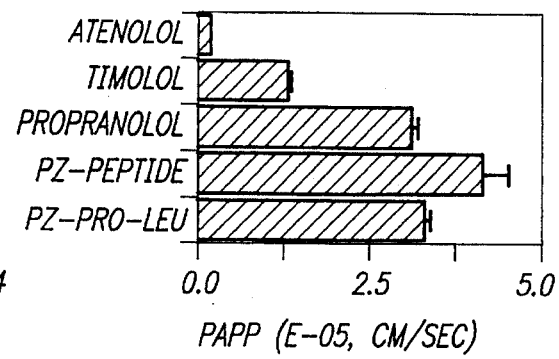
Figure 3B:
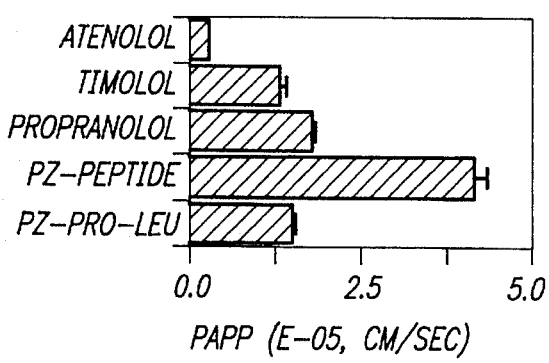
Figure 3E:
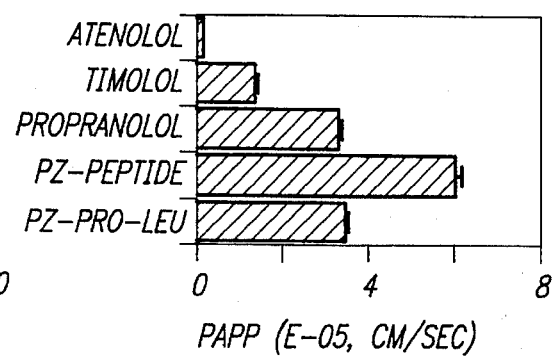
Figure 3C:
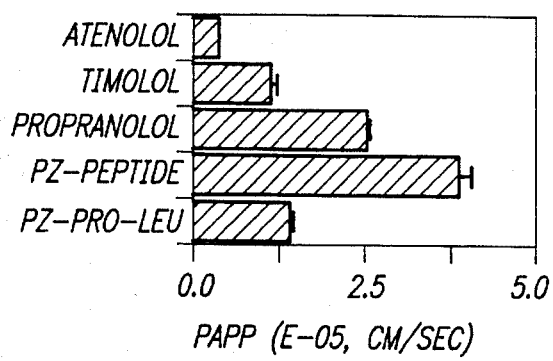
Figure 3F:
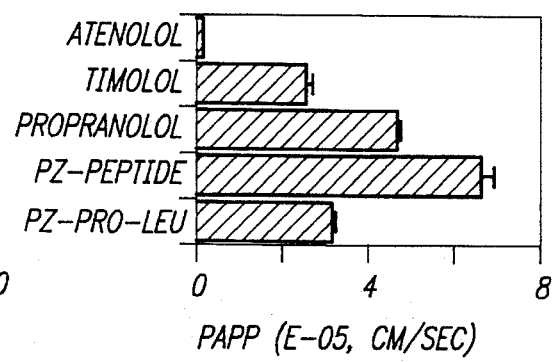
Figure 4:
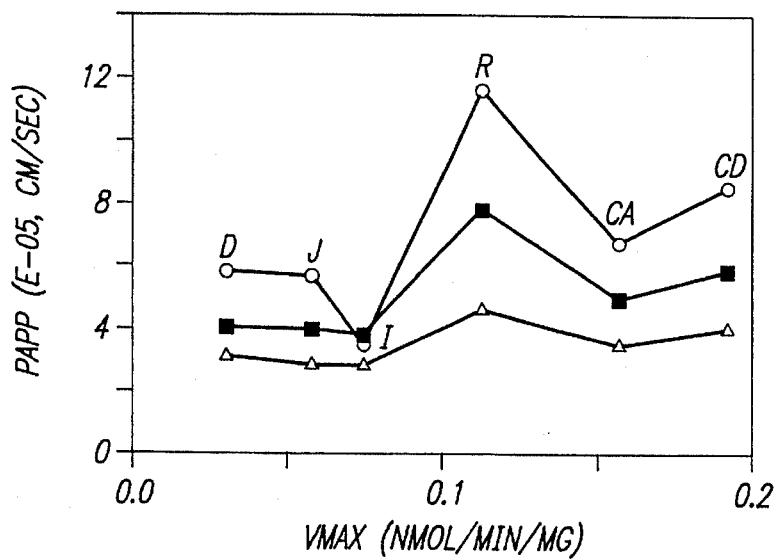
FIG. 4 shows the correlation between collagenase activity (Vmax) and extent of Pz-peptide penetration (Papp) described in Example 3. Key: △, 1 mM; ■, 3 mM; ○, 5 mM. Error bars are omitted for clarity.

In spite of high collagenase activity seen in the cytosol, Pz-peptide was able to penetrate all the intestinal segments to varying extents as determined by the procedure described in section B above. For example, although collagenase activity was highest in the descending colon, Pz-peptide penetrated the second best in this region with more than 80% of it in the intact form (FIG. 2). The lower intestine was more permeable to Pz-peptide than the upper intestine. In the upper intestine, the duodenum, jejunum and ileum were equally permeable to this peptide. In the lower intestine, the rank order of permeability coefficient was rectum>descending colon>ascending colon. Furthermore, despite their hydrophilic character as indicated by a low distribution coefficient determined by the procedure described in section D above, for Pz-peptide (3.65±0.08) and Pz-product (4.34±0.14), both compounds penetrated equally well or even better than atenolol (DC=1.46), timolol(DC=82) and propranolol (DC=1640) (Betageri, G. V. and Rogers, J. A.(1987) Int. J. Pharm. 36, pp. 165–173) of higher DC in all intestinal segments (FIG. 3). Presumably, Pz-peptide was transported across the intestinal mucosa mainly by the paracellular pathway and may have some effects on the tight junctions. Such a possibility was supported by the observation that the expected inverse correlation between extent of Pz-peptide penetration and collagenase activity was not obtained (FIG. 4).

EXAMPLE 3

Figure 5A:
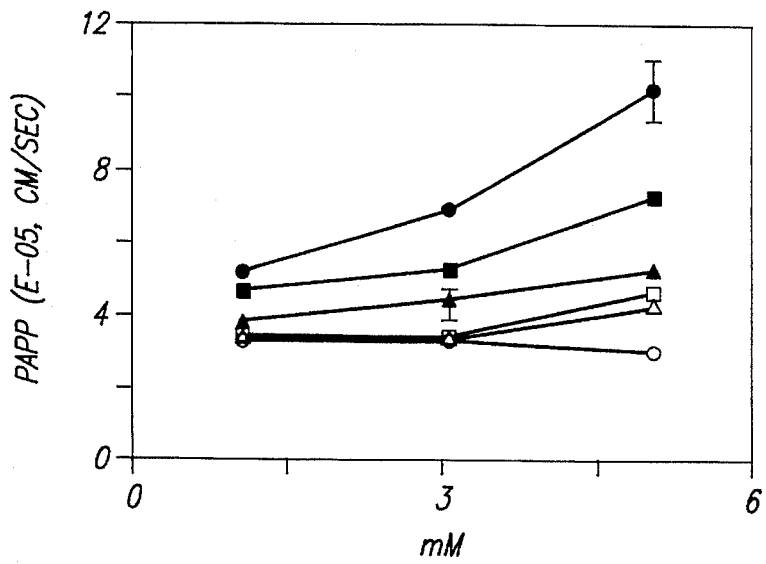
FIGS. 5A–5B show the concentration dependence of Papp of Pz-peptide (FIG. 5A) and Pz-Pro-Leu(FIG. 5B) described in Example 4. Error bars represent s.e.m. for n=3. Key △, Duodenum; □, Jejunum; ○, Ileum; ▲, Ascending colon; ■, Descending colon; and ●, Rectum.
Figure 5B:
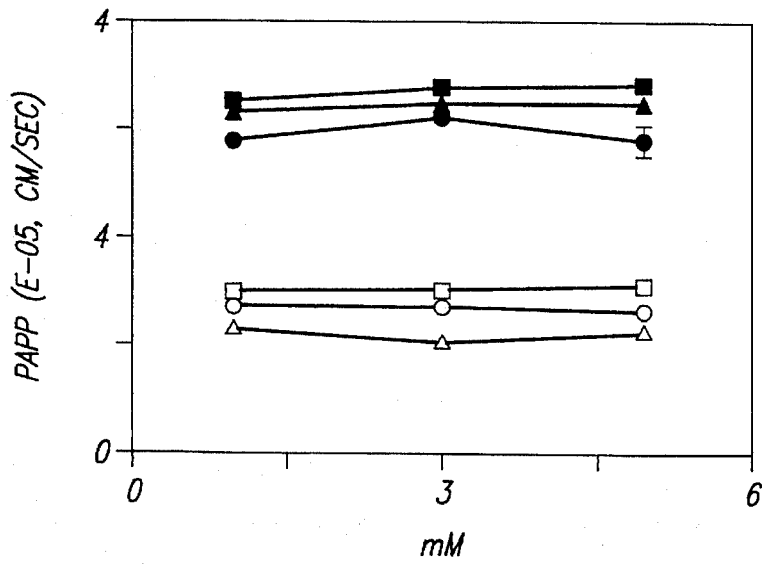
Figure 6A:
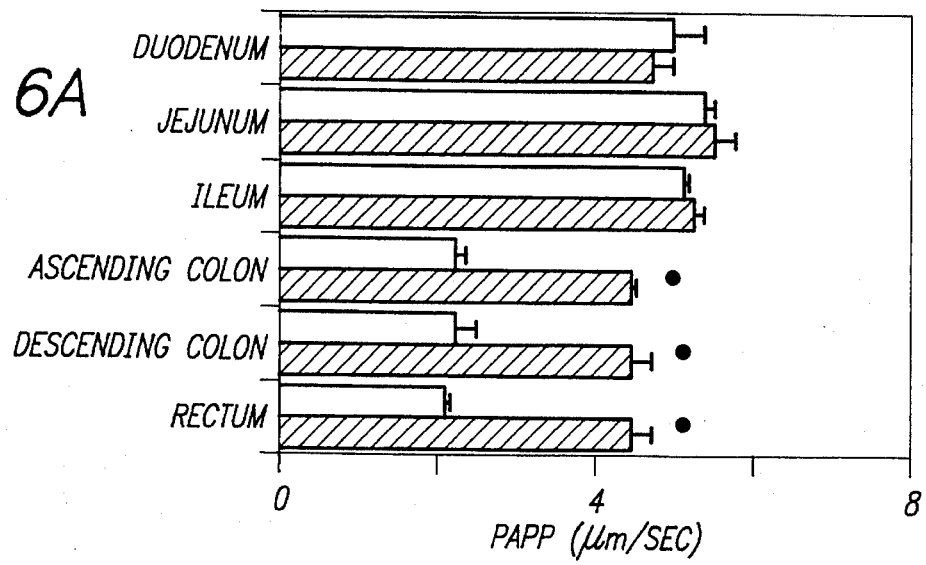
FIGS. 6A–6B show the effect of 3 mM Pz-peptide on the intestinal penetration of mannitol (FIG. 6A) and atenolol (FIG. 6B). Key: □, control; ■, with 3 mM Pz-peptide described in Example 4. Error bars represent s.e.m. for n=3. Asterisks denotes statistical significance at $p<0.05$ by Student's t-test.
Figure 6B:
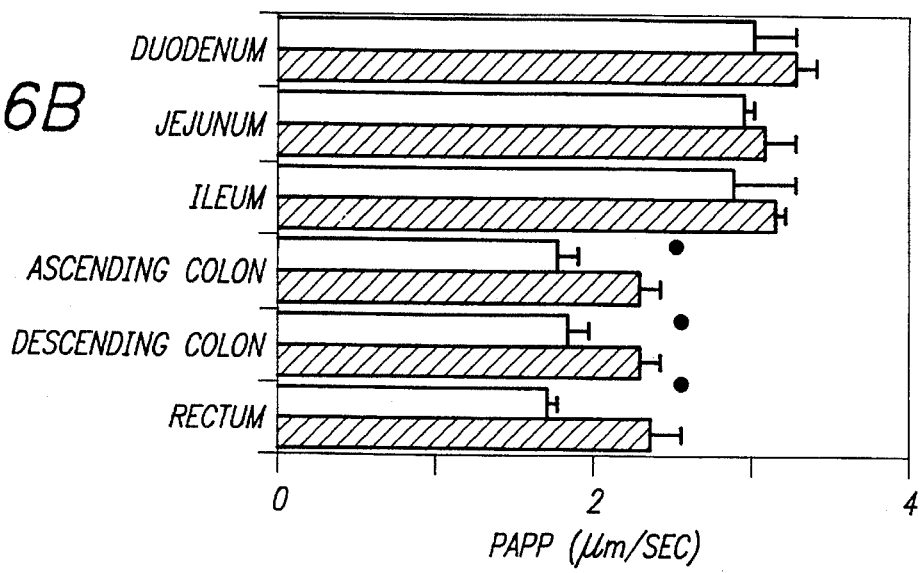
Figure 7:
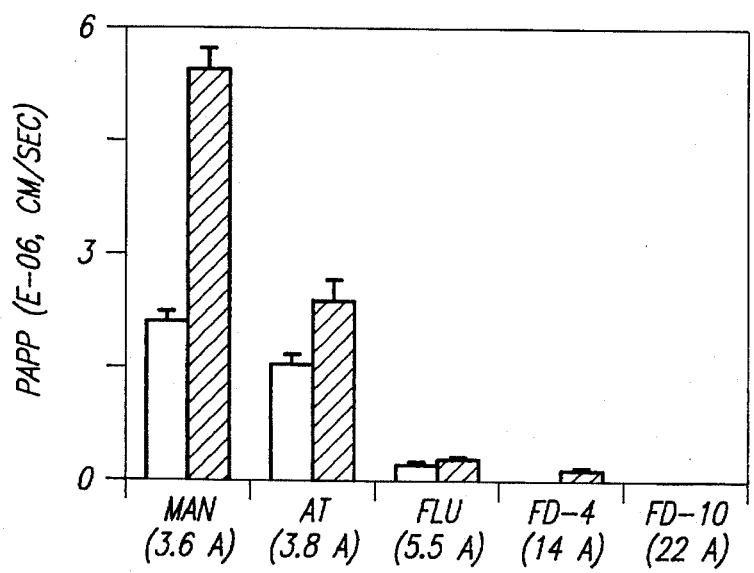
FIG. 7 shows the effect of Pz-peptide on penetration of paracellular markers mannitol (Man, 3.6 A), atenolol (At, 3.8 A), fluorescein (FLu, 5.5 A), FITC-dextran 4,000(FD-4, 14 A) and FITC-dextran 10,000 (FD-10, 22 A) described in Example 5. Key □, control; ■, with 3 mM Pz-peptide. Error bars represent s.e.m. for n=3.
Figure 10C:
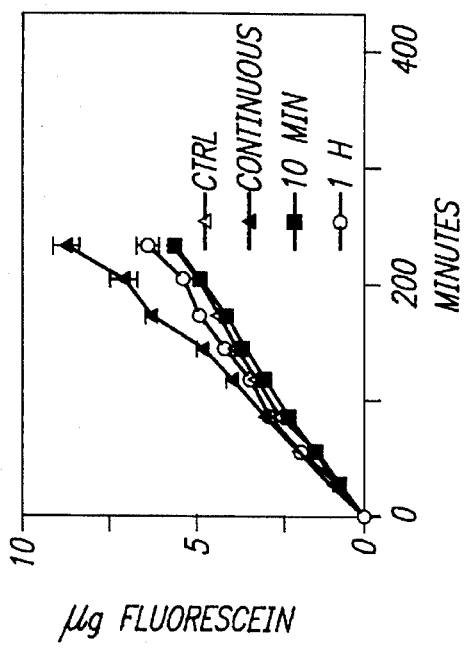
FIGS. 10A–10D show the effect of exposure time on penetration of mannitol (FIG. 10A), atenolol (FIG. 10B), fluorescein (FIG. 10C) and FITC-dextran 4,000 (FIG. 10D), all at 3 mM Pz-peptide described in Example 7. Key: Δ, control; ■, continuous; ○, 10 min. exposure; , 1 hour exposure. Error bars represent s.e.m. for n=3.
Figure 10D:
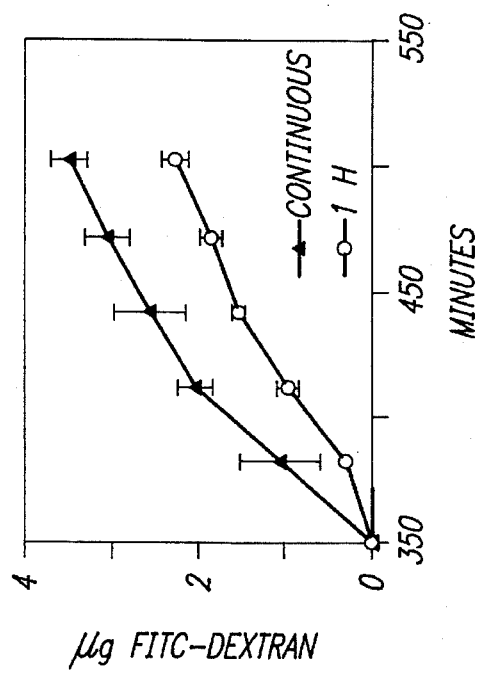
Figure 10A:
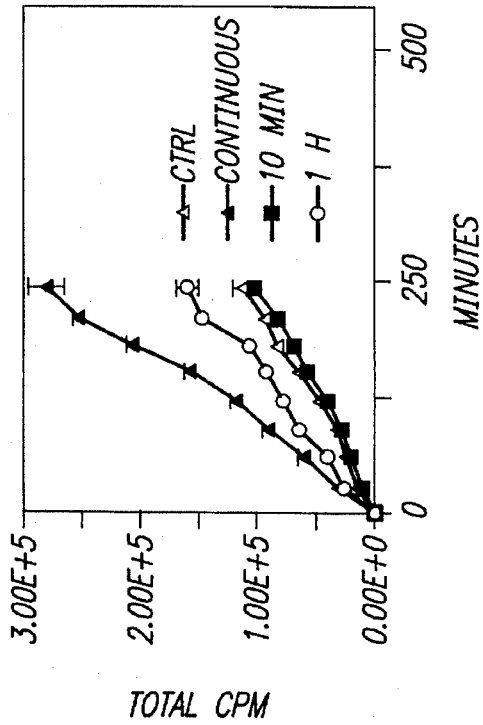
Figure 10B:
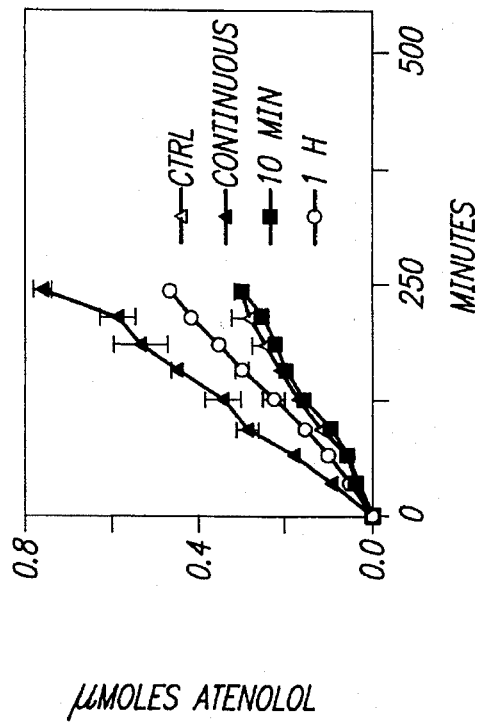

Determination of intestinal transport of the pz-peptide as a function of Pz-peptide concentration The transport of Pz-peptide was independent of concentrations in the range of 1–5 mM in the upper G.I. segments. However, penetration increased with increasing peptide concentrations in the lower G.I. regions. On the other hand, penetration of Pz-Pro-Leu was independent of concentrations in all intestinal segments studied (FIG. 5). The hypothesis that Pz-peptide transported by the paracellular pathway and affected junctional permeability was further confirmed by a Pz-peptide induced increase in the penetration of paracellular markers mannitol and a hydrophilic β-blocker atenolol in the lower G.I. segments (FIG. 6).

EXAMPLE 4

Enhancement of drug transport by the Pz-peptide

The effect of Pz-peptide on extent of paracellular permeability was studied in human colon carcinoma cell monolayer as described above in section C. Five paracellular markers with different molecular radii were used to determine the extent of enhancement. Pz-peptide at 3 mM was able to enhance transport of mannitol (3.6 A), atenolol (3.8 A), fluorescein (5.5 A) and FITC-dextran 4,000 (FD-4, 14 A) by a factor from 1.5 to 10 (FIG. 7), while no enhancement was found in FITC-dextran 10,000 (FD-10, 22 A) by Pz-peptide.

EXAMPLE 5

Enhancement of drug transport by the Pz-peptide as a function of concentration

The increased transport of paracellular markers by Pz-peptide is found to be concentration-dependent (FIG. 8). Furthermore, such increase in penetration was correlated with decrease in transepithelial electrical resistance, TEER, induced by Pz-peptide at various concentration (FIG. 9). However, Pz-peptide was unable to induce transport of FD-10, a marker with a molecular radius>14 Å, in all concentrations studied.

EXAMPLE 6

Enhancement of drug transport by the Pz-peptide as a function of time

To determine the minimum exposure time required by Pz-peptide to increase junctional permeability, cells were exposed to Pz-peptide for various time periods. As shown in FIG. 10 that there was no effect on marker transport for 10-minute exposure; however, about 65% to 9-fold increase in transport was found after one hour exposure. The extent of enhancement was further increased by prolonged exposure.

EXAMPLE 7

Comparison of enhancement effect by Pz-peptide, EDTA and Cytochalasin B

Figure 11A:
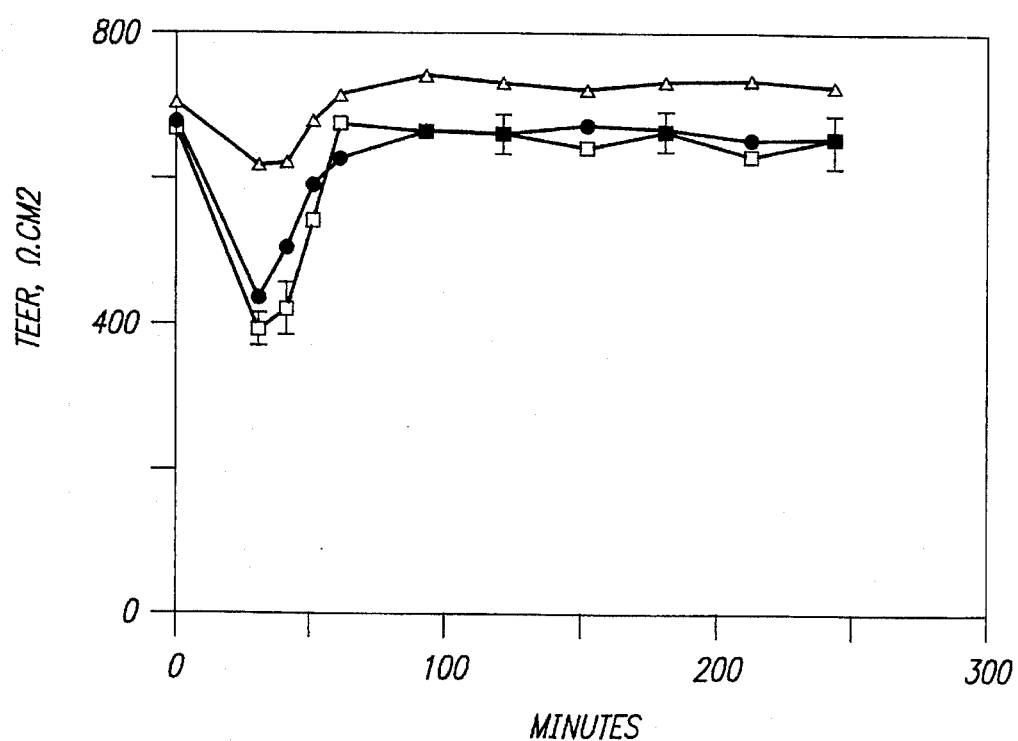
FIGS. 11A–11B show the time-dependent reversibility of TEER by Pz-peptide, EDTA and cytochalasin B at 30 min.
Figure 11B:
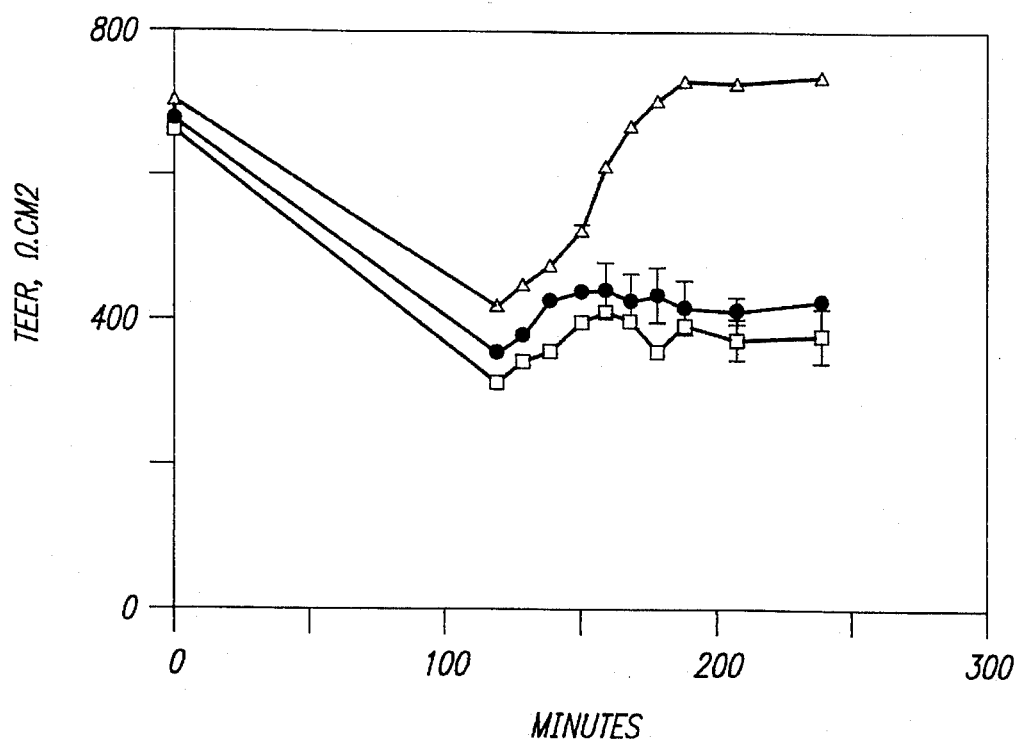
Figure 12A:
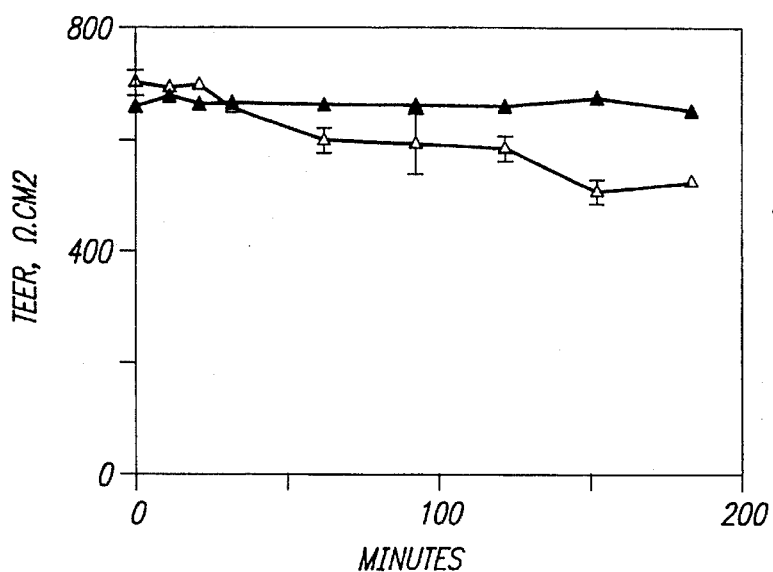
FIGS. 12A–12C show the effect of apical and basolateral applications of Pz-peptide (FIG. 12A), EDTA (FIG. 12B) and cytochalasin B (FIG. 12C) on TEER measurements, all at 3 mM described in Example 8. Key: Δ, apical application; ▲, basolateral application. Error bars represent s.e.m. for n=3.
Figure 12B:
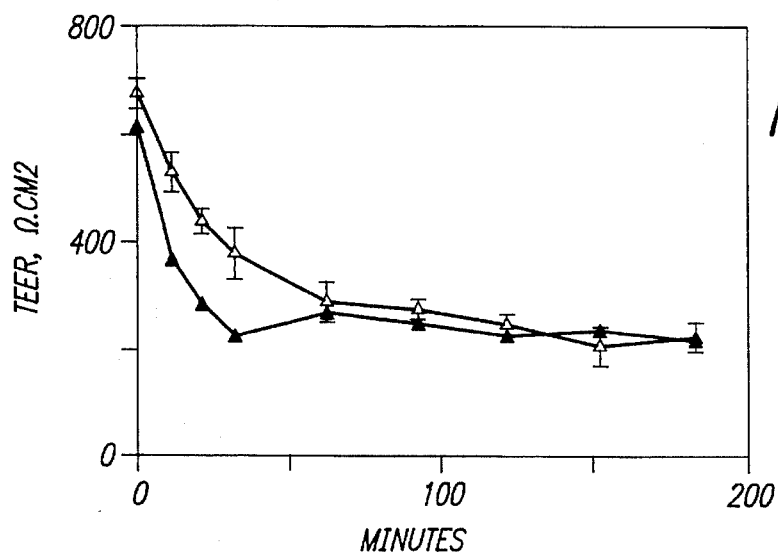
Figure 12C:
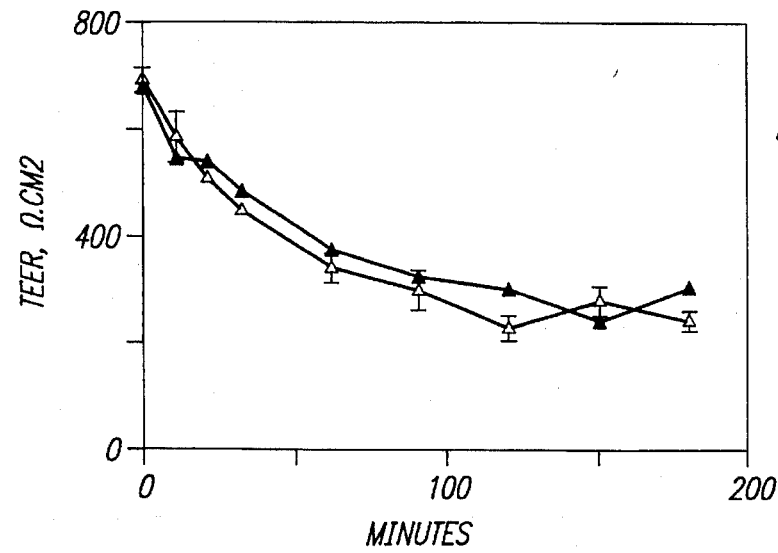

To determine the cellular locus where Pz-peptide exerts its enhancement effect, two paracellular penetration enhancers with known mechanism of action were used as references. EDTA is known to increase junctional permeability by chelating the intracellular $Ca^{+2}$ level (Cassidy, M. M. and Tidball, C. S. (1967) J. Cell Biol. Vol. 32, p. 685), whereas cytochalasin B is known to inhibit the polymerization of actin filament (Meza, I. G. et al. (1980) J. Cell Biol. Vol. 87, p. 746). As shown in FIG. 11, exposure of cells to all three enhancers at 3 mM showed a time-dependent reversibility of TEER with increasing exposure time. In the case of Pz-peptide, TEER was fully restored by replacing calcium-containing buffer at both short and long-term exposure. On the other hand, prolonged exposure of the cells to either EDTA or cytochalasin B resulted in only partial recovery of TEER (FIG. 11). Such a different mechanism of action found in these three enhancers was further confirmed by different TEER via apical or basolateral applications. Pz-peptide was able to decrease TEER only by apical application. The effect of EDTA on TEER was more pronounced by basolateral application, whereas cytochalasin B exerted similar effect on TEER by either applications (FIG. 12).

Based on the above findings it appears that the effect of Pz-peptide on junctional permeability was not by removal of intracellular $Ca^{+2}$ nor by contraction of actin filaments. The possibility of Pz-peptide acted as a surfactant was further excluded since there was (a) no decrease in surface tension activity in all concentrations tested and (b) no effect on membrane fluidity as indicated by no significant spectra changes caused by Pz-peptide at 5 mM in the electron spin resonance with either a surface lipid probe 5-doxyl stearic acid(5-DSA) or an inner probe 16-doxyl stearic acid (16-DSA) incorporated in brush border membrane vesicles prepared from both upper and lower G.I. segments.

EXAMPLE 8

Pz-peptide's influence on sodium channel

Figure 13A:
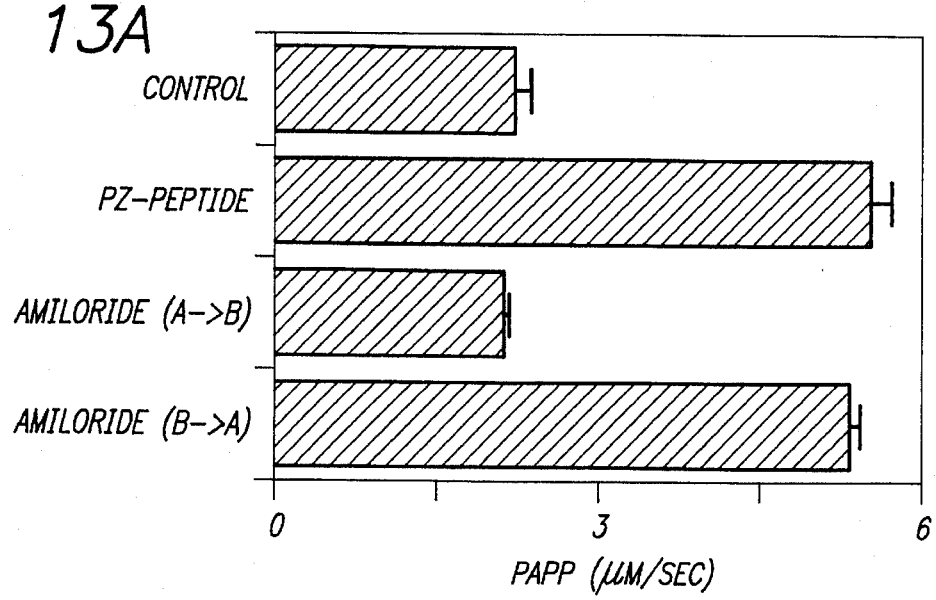
FIGS. 13A–13B show the effect of apical and basolateral applications of 10 μM amiloride, a sodium channel blocker on penetration of mannitol (FIG. 13A) and 3 mM Pz-peptide (FIG. 13B) described in Example 9. Error bars represent s.e.m. for n=3.
Figure 13B:
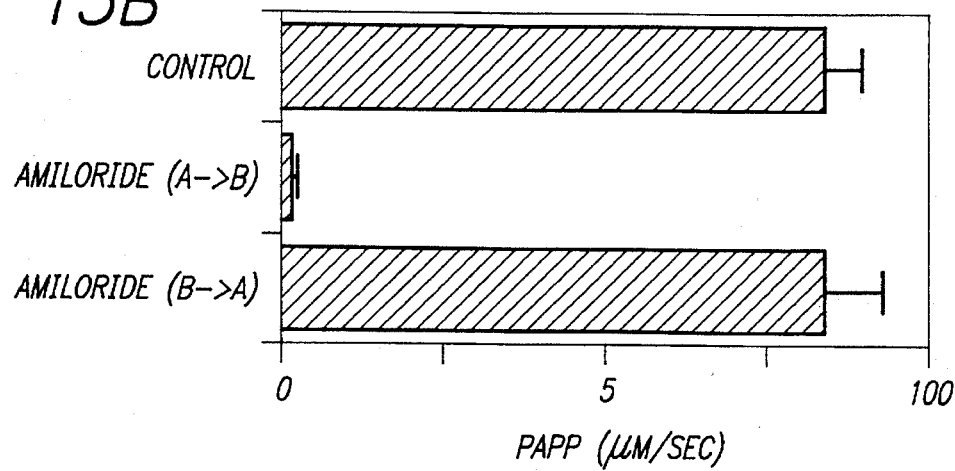
Figure 14:
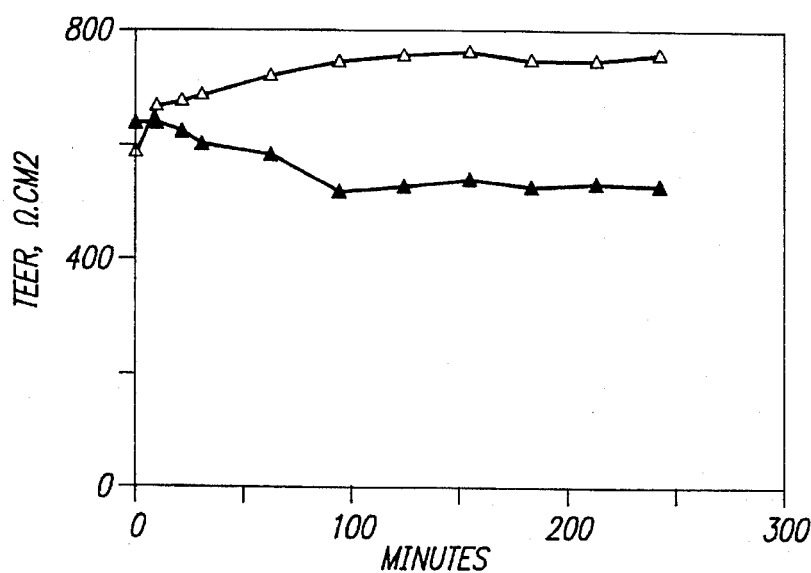
FIG. 14 shows the effect of apical and basolateral applications of 10 μM of amiloride on TEER measurements described in Example 9. Both measurements were conducted in the presence of 3 mM Pz-peptide on the apical side. Key: Δ, apical application; ▲, basolateral application. Error bars represent s.e.m. for n=3.

It is known that electrogenic $Na^+$ absorption is predominant in the colon by means of $Na^+$ channels on the apical membrane (Grady, G. F. et al. (1970) Gastroenterology, Vol 19, p. 583). To further determine whether the effect of Pz-peptide on junctional permeability in the lower G.I. segments was via activation of $Na^+$ channels, a sodium channel blocker amiloride was used. Amiloride at 10 µM abolished both Pz-peptide-induced mannitol transport as well as its own penetration in Caco2 monolayers when applied to the apical side. Such effect was not seen when amiloride was applied to the basolateral side (FIG. 13). These results were further confirmed by TEER measurements (FIG. 14).

EXAMPLE 9

Role of the N-terminal Pz-group

Figure 15:
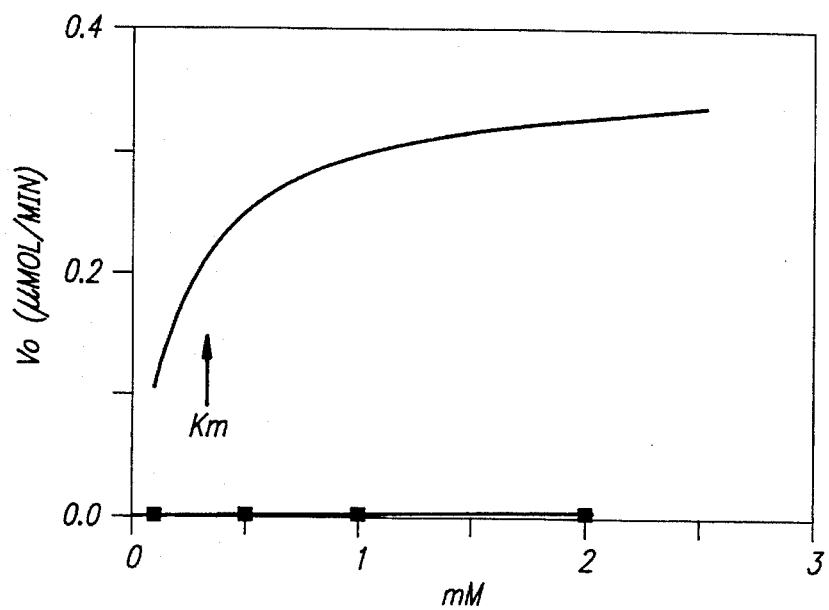
FIG. 15 shows hydrolysis of Pz-peptide and PLEP$^d$R to 0.04 mg/ml bacterial collagenase described in Example 10. Key: ■, Pz-peptide; ■, PLEP$^d$R.
Figure 16:
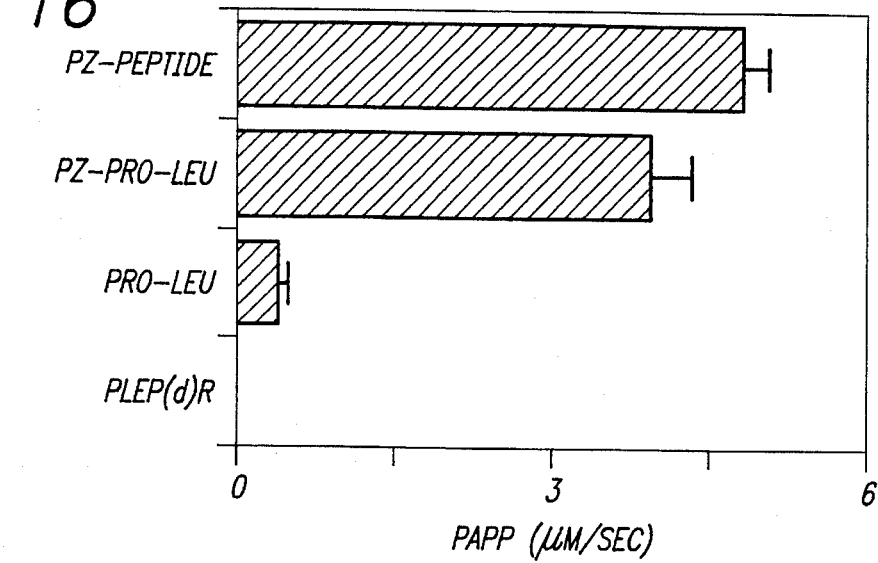
FIG. 16 shows the extent of penetration (Papp) of Pz-peptide, Pz-Pro-Leu, Pro-Leu and PLEP'R across Caco2 monolayers, all at 5 mM described in Example 10. Error bars represent s.e.m. for n=3.
Figure 17:
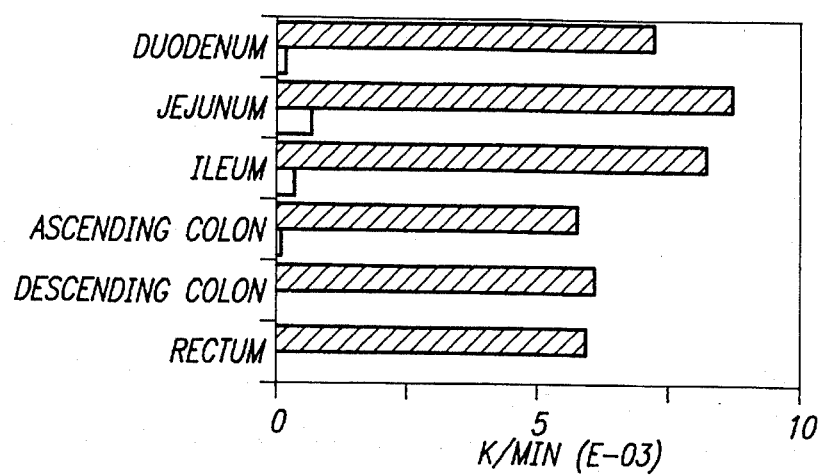
FIG. 17 shows the degradation rate constant of Pz-Pro-Leu and Pro-Leu in various intestinal homogenates, both at 0.5 mM described in Example 10. Key: □, Pz-Pro-Leu; ■, Pro-Leu.

To establish the role of the N-terminal Pz-group on facilitating penetration of Pz-peptide and Pz-Pro-Leu two non-Pz analogues, PLEP$^d$R [SEQ ID NO: 3] and Pro-Leu were used to study their enzymatic stability and penetration across the Caco2 monolayers as described in section E above. Although PLEP$^d$R [SEQ ID NO: 3] was not susceptible to collagenase action, as indicated by a much smaller initial velocity, Vo, relative to Pz-peptide (FIG. 15), no direct peptide was detected in the mucosal side of the Caco2 monolayers. Similarly, penetration of Pro-Leu was about 10 times lower than Pz-Pro-Leu (FIG. 16). Unlike Pz-Pro-Leu, which was resistant to enzymatic degradation, Pro-Leu was degraded to various extent in the intestinal homogenates (FIG. 17).

The foregoing description of the invention has been directed to particular preferred embodiments for purposes of explanation and illustration. It will be apparent, however, to those skilled in the art, that many modifications and changes in the particular methods, materials and methods of use may be made without departure from the scope and spirit of the invention. It is applicants' intention in the following claims to cover all such equivalents, modifications and changes that fall within the true spirit and scope of the invention.

---

What is claimed is:

1. A method for enhancing the delivery of a drug across epithelial cells at a mucosal site comprising:
   (a) introducing a peptide to said mucosal site either concomitant with or prior to administration of said drug or
   (b) introducing to said mucosal site a peptide which is covalently bonded to said drug;
   wherein said peptide is selected from the group consisting of Pro-Leu-Gly-Pro-Arg [SEQ ID NO: 4], Pro-Leu-Gly-Pro-Lys [SEQ ID NO: 6], Pro-Leu-Gly-Pro-Glu [SEQ ID NO: 7], Pro-Leu-Gly-Pro-Asp [SEQ ID NO: 8], Pro-Leu-Gly-Pro [SEQ ID NO: 5], Pro-Leu-Gly and Pro-Leu, and having a protective group selected from the group consisting of Pz-, N-methyl, t-Boc, FMOC and CBZ at the N-terminus of said peptide to the mucosal site by an oral, nasal, pulmonary, buccal, rectal, transdermal, vaginal or ocular route in an amount sufficient to enhance the transport of said drug across epithelial cells at the mucosal site.

2. A method according to claim 1 wherein the drug and peptide are mixed prior to introducing said drug and said peptide to the mucosal site.

3. A method according to claim 1 wherein said enhanced drug delivery is achieved by administering the drug covalently attached to said peptide.

4. A method according to claim 1 wherein said drug and said peptide are introduced to the mucosal site by a microcapsule, microsphere, liposome, cell, bacteria or food vesicle carrier.

5. A method according to claim 1 wherein said drug and said peptide are introduced to the mucosal site simultaneously.

6. A method according to claim 1 wherein said peptide is first introduced to the mucosal site prior to the introduction of said drug.

7. A method according to claim 1 wherein said drug is selected from the group consisting of an insulin, a vasopressin, a leucine enkephalin, Asu-eel calcitonin, 5-fluorouracil, a salicylamide, a β-lactone, an ampicillin, a penicillin, a cephalosporin, a β-lactamase inhibitor, a quinolone, a tetracycline, a macrolide, a gentamicin, acyclovir, ganciclovir, a trifluoropyridine, and pentamidine.

8. A pharmaceutical composition for enhancing delivery of a drug across epithelial cells at a mucosal site comprising
   a Pro-Leu-Gly-Pro-Arg [SEQ ID NO: 4] peptide with a Pz-group at the N-terminus of said peptide, said peptide further present in an amount of 0.1–10 mg;
   a cyclodextrin carrier coating in which said peptide is dispersed and within which a drug selected from the group consisting of mannitol, atenolol, fluorescein, an insulin, a vasopressin, leucine enkephalin, Asu-eel calcitonin, 5-fluorouracil, a salicylamide, a β-lactone, an ampicillin, a penicillin, a cephalosporin, a β-lactamase inhibitor, a quinolone, a tetracycline, a macrolide, a gentamicin, acyclovir, ganciclovir, a trifluoropyridine, and pentamidine is entrapped.

* * * * *